United States Patent
Amirault et al.

(10) Patent No.: US 9,278,665 B2
(45) Date of Patent: Mar. 8, 2016

(54) SLOUCH CORRECTION DEVICE AND METHOD

(71) Applicant: Nova Scotia Community College, Halifax (CA)

(72) Inventors: Dustin Joseph Amirault, Halifax (CA); Joshua Douglas Matthews, Calgary (CA); Jamison Stuart Etter, Halifax (CA); Shaemus Mullaney, Halifax (CA); Matthew MacKenzie, Minevilline (CA); Gail Giffin, Halifax (CA)

(73) Assignee: NOVA SCOTIA COMMUNITY COLLEGE, Halifax (CA)

( * ) Notice: Subject to any disclaimer, the term of this patent is extended or adjusted under 35 U.S.C. 154(b) by 0 days.

(21) Appl. No.: 13/900,016

(22) Filed: May 22, 2013

(65) Prior Publication Data

US 2013/0320746 A1 Dec. 5, 2013

Related U.S. Application Data

(60) Provisional application No. 61/652,497, filed on May 29, 2012.

(51) Int. Cl.
| | |
|---|---|
| *A47C 31/11* | (2006.01) |
| *B60R 22/00* | (2006.01) |
| *A61F 5/37* | (2006.01) |
| *A61G 5/10* | (2006.01) |
| *A61G 5/12* | (2006.01) |

(52) U.S. Cl.
CPC ............... *B60R 22/00* (2013.01); *A61F 5/3776* (2013.01); *A61F 5/3792* (2013.01); *A61G 2005/1045* (2013.01); *A61G 2005/1054* (2013.01); *A61G 2005/124* (2013.01)

(58) Field of Classification Search
USPC ............ 297/228.12, 464, 465, 485, 487, 488, 297/228, 228.1, 228.11, 228.13, 229
See application file for complete search history.

(56) References Cited

U.S. PATENT DOCUMENTS

| | | | | |
|---|---|---|---|---|
| 4,073,537 A | * | 2/1978 | Hammersburg | ............... 297/464 |
| 4,541,425 A | * | 9/1985 | Yetter, Jr. | .................. 297/464 X |
| 4,676,376 A | * | 6/1987 | Keiswetter | ............. 297/228.1 X |
| 4,884,839 A | * | 12/1989 | Keiswetter | ................ 297/229 X |
| 5,123,699 A | * | 6/1992 | Warburton | ................ 297/464 X |
| 5,148,563 A | * | 9/1992 | Klearman et al. | ......... 297/465 X |
| 5,154,487 A | * | 10/1992 | Warburton | .................... 297/465 |
| 5,426,801 A | * | 6/1995 | Klearman et al. | ......... 297/465 X |
| 5,452,476 A | * | 9/1995 | Jenks | ..................................... 2/46 |
| 5,496,092 A | * | 3/1996 | Williams et al. | .......... 297/464 X |
| 5,626,397 A | * | 5/1997 | Reid | ........................... 297/485 X |
| 5,628,548 A | * | 5/1997 | Lacoste | ..................... 297/464 X |
| 5,669,671 A | * | 9/1997 | Laco | .............................. 297/485 |

(Continued)

*Primary Examiner* — Rodney B White
(74) *Attorney, Agent, or Firm* — Young Law Firm, P.C.

(57) ABSTRACT

A slouch correction device and a method of operation is provided for use in a chair, in which the slouch correction device is predominantly a loose seat cover on which a patient would sit, one or more straps from the seat cover which pass through an opening between the chair back and seat to secure to a separate harness or to form a harness about the waist of a caregiver, such that a care giver is able to pull on the harness to slide the seat cover and patient seated thereon back into an improved, upright posture position, while using free hands to hold the chair in a steady position. The slouch correction device provided with various improvements, including dual side handles for two person lifts, means to keep straps in safe and easily accessed position when not in use, and comfort features on the harness.

12 Claims, 7 Drawing Sheets

(56) References Cited

U.S. PATENT DOCUMENTS

| | | | |
|---|---|---|---|
| 5,709,431 A * | 1/1998 | Horn | 297/228.1 |
| 5,896,603 A * | 4/1999 | Cooper | 297/228.11 X |
| 6,067,777 A * | 5/2000 | Stoll | 297/228.1 X |
| 6,082,826 A * | 7/2000 | Moreno | 297/464 |
| 6,212,717 B1 * | 4/2001 | Cooper | 297/228.11 X |
| 6,378,947 B1 * | 4/2002 | Barber et al. | 297/488 X |
| 6,513,824 B2 * | 2/2003 | DuBose | 297/465 X |
| 6,616,225 B2 * | 9/2003 | Graff | 297/229 |
| 6,648,410 B2 * | 11/2003 | Sparks | 297/228.12 |
| 6,676,209 B1 * | 1/2004 | Szabo et al. | 297/228.13 X |
| 6,840,577 B2 * | 1/2005 | Watkins | 297/464 X |
| 7,097,628 B1 * | 8/2006 | Baune | 297/464 X |
| 7,237,848 B1 * | 7/2007 | Story et al. | 297/485 |
| 7,316,451 B2 * | 1/2008 | Balensiefer et al. | 297/464 X |
| 7,458,104 B1 * | 12/2008 | Garcia | 2/69.5 |
| 7,574,751 B2 * | 8/2009 | Barreiro | 2/88 |
| 7,926,881 B1 * | 4/2011 | Youreman | 297/464 |
| 8,007,046 B2 * | 8/2011 | Rothschild | 297/485 |
| 8,950,807 B2 * | 2/2015 | Lerm | 297/228 X |
| 2003/0085598 A1 * | 5/2003 | Monday | 297/228.12 |
| 2005/0194830 A1 * | 9/2005 | Kohani | 297/464 |
| 2007/0085408 A1 * | 4/2007 | Kohani | 297/465 |
| 2009/0152932 A1 * | 6/2009 | Rothschild | 297/465 |
| 2011/0049951 A1 * | 3/2011 | Bettencourt | 297/229 |
| 2011/0272995 A1 * | 11/2011 | Rothschild | 297/465 |
| 2014/0223666 A1 * | 8/2014 | Pavlin | 297/229 X |

* cited by examiner

SLOUCH CORRECTION DEVICE AND METHOD

FIELD

The present disclosure relates to aids, methods, devices and apparatus to assist caregivers in adjusting the position and posture of patients or invalids in chairs.

BACKGROUND

A common problem identified in long term care facilities is the worsening of posture of wheel chair bound patients, and harm to caregivers seeking to adjust and improve patient posture.

Slouching is a natural occurrence in wheel chair users, with known negative consequences. The neck and back muscle begin to stiffen and becomes very uncomfortable. Not only is the position uncomfortable but it is also un-dignifying to invalid wheelchair users having to be in that position for extended period of time. However, the ability to correct posture requires effort on the part of the patient or the caregiver.

Restraints and constraints are imperfect, and the long term care industry is leaning away from constraints in wheelchairs as a means to prevent poor posture.

From a caregiver perspective the slouching presents a problem of time and the potential for injury. One existing method to correct posture is to use a two person procedure to reposition the wheel chair user. This takes extra time and an extra caregiver who could be doing another assigned task. Another method is to use products that are designed to prevent patients from sliding forward, such as the uni-directional friction pad sold under ERGOGLIDE 5300™, by ErgoSafe Products, and form fitting gel, memory foam or molded seat cushions.

However, patients inevitably slide forward, when unrestrained, and when they do, the above products still require the caregiver to use upper body and back muscles to do the majority of the work in repositioning the invalid patient. This action increases the probability of injury to the caregiver. As such, the current methods and products for repositioning are ineffective and pose hazards of injury to the caregiver and wheel chair user.

There is a need for a reposition, slouch correction device and method which permits a single caregiver to use leg muscles to provide slouch correcting repositioning to a person in a chair.

There is a need for a patient slouch correcting device which improves patient and caregiver safety, comfort and dignity.

There is a need for a patient slouch correcting device which is able to withstand industrial washing and repeated use.

SUMMARY

A slouch correction device, or the aid, is provided for use in a chair, in which the slouch correction device is predominantly a loose seat cover on which a patient would sit, one or more straps from the seat cover which pass through one or more openings between the chair back and seat to secure to or form a harness about the waist of a caregiver, such that a care giver is able to use pull on the harness to slide the seat cover and patient seated thereon back into an improved, upright posture position.

Optionally, the slouch correction device may be further provided with side folds and lateral hand holds to permit two person lifting, or to facilitate use by a single user.

The straps are secured to a harness about the caregiver, which may be a belt, adjustable loop, or attachment means to detachably attach from each other to form a belt about a care giver. Alternatively, the straps from the sling/seat cover of the aid may be provided with attachment means for detachably attaching to corresponding attachment means on a harness or belt worn by the caregiver. Such attachment means may include, Velcro, male/female clipping attachments or interconnections, ladder locks, belt buckles, backpackers slide, snaps, or the like.

The harness about the caregiver is either detachable from the straps, or formed by the straps wrapping around the caregiver to detachably form a secure loop.

This device has potential to eliminate injury due to this task, allows the wheel chair user to be positioned quickly, and/or allows the wheelchair user to be repositioned without direct physical contact from the caregiver.

The device may be laid on any chair, including a wheelchair, having one or more openings between the chair seat and the chair back. The straps are passed through the one or more openings of the chair. The seat cover portion is made of a material such that a top side of the seat cover has a higher expected co-efficient of friction between the top side and the patient than the bottom side of the seat cover has with the chair seat. In this fashion, the device slides with the patient when the patient slides. When a patient slides forward into a forward slouching position with the patient's posterior away from the chair back, a caregiver attaches the straps to a harness about his or her waist, and is able to use free hands to hold the chair or the patient, while moving hips and legs backwards to slide the patient into a preferred position. The steps of the method are:

Step 1: lay the seat cover portion of the device on a chair seat with top side up, and straps passed through one or more dorsal openings on the chair;

Step 2: seat a person on the chair;

Step 3: when the person slides forward with the device, stand behind chair and attach the straps about body to form harness or clip to interconnections on strap to interconnections on separately provided harness. Optionally, the operator of the method may adjust the seated persons arms and legs to a safer position during this step;

Step 4: Adjust straps to appropriate length;

Step 5: hold the chair with free hands; and

Step 6: use leg muscles to pull device and person seated thereon back into chair while holding chair in steady position.

The method prefers a device formed of resilient materials in order to permit repetitive application of the tensile forces needed to move patients, some of whom may be quite heavy.

The slouch correction device is for use by a patient seated on a chair having a chair seat, chair back and dorsal opening between the chair seat and chair back, and by a caregiver. The slouch correction comprises a seat cover portion for positioning on the chair seat having one or more reward facing straps and a harness detachably attachable to the rearward straps. Although only two straps are shown in the drawings, one strap or a plurality of straps feeding to one or more straps may also be included with this disclosure. The harness may be a belt, or may be provided with additional clips or comfort features for a caregiver using the aid. Optionally, the seat cover may be a reinforced textile mat. Optionally, the rearward straps may have harness interconnection pieces thereon for interconnection to strap interconnections on the harness, or may simply slip around the harness and secure to themselves, or be secured and tightened in some other known manner using clips or buckles on the harness. Optionally, the seat cover portion has side panels to form a sling shape, and one or more handles on either side portion can facilitate a two person lift, and dual handle holds on each side permit each person in a two person lift to use both hands without the hand holds bunching together.

When not in use, the straps may be detachably attached to interconnection on the back of the chair.

DETAILED DESCRIPTION

The preferred embodiments of the slouch correction device will now be explained in greater detail with reference to the accompanying figures.

EXAMPLE 1

Figure 1:
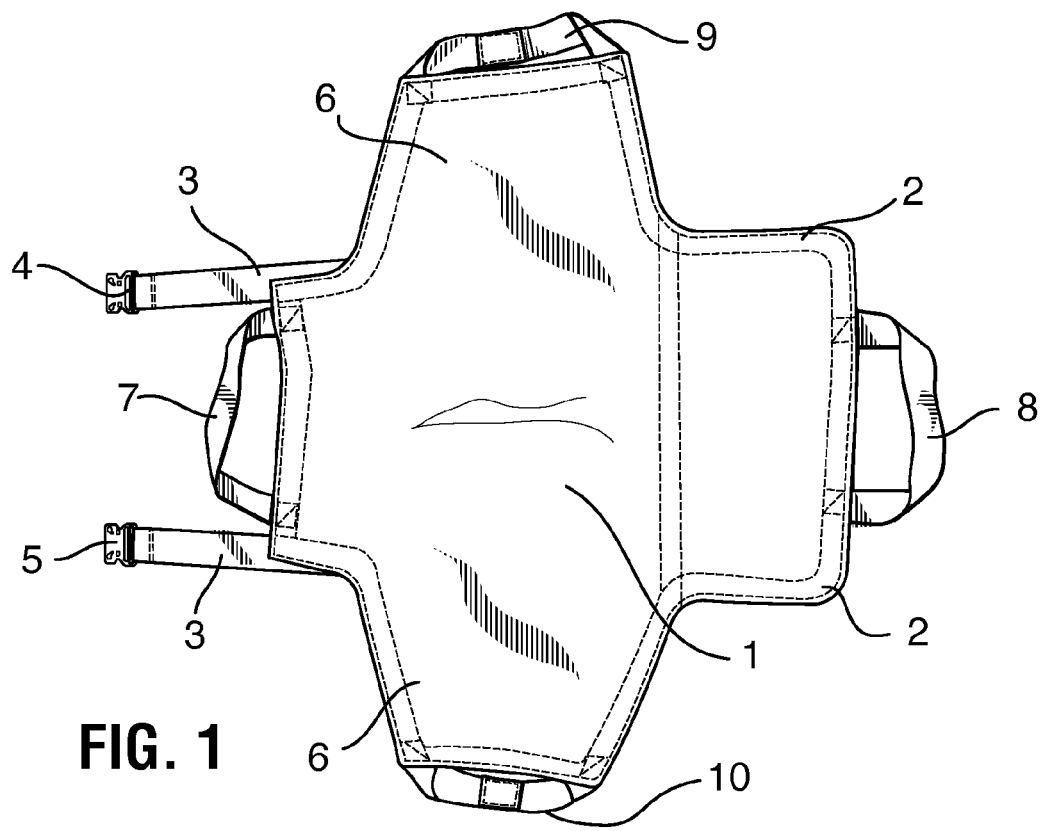
FIG. 1 is a top view of one example of the sling/seat cover portion of the slouch correction device.
Figure 2:
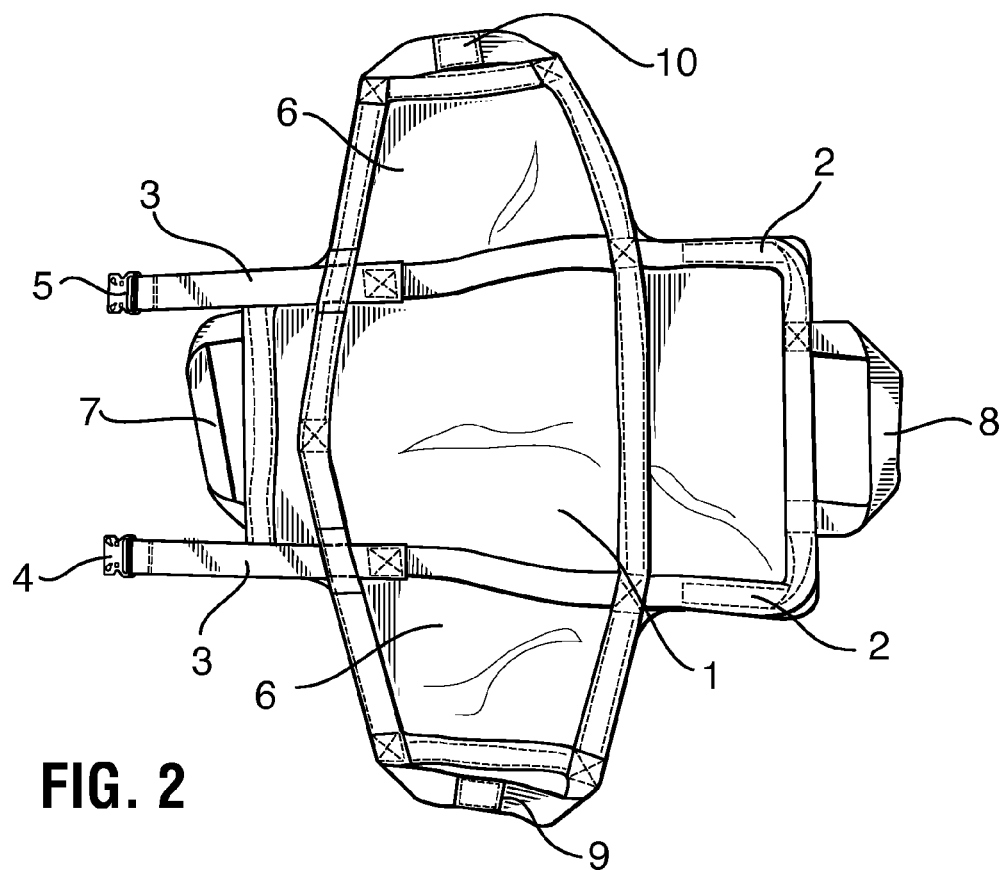
FIG. 2 is a bottom view of the sling/seat cover portion of the slouch correction device of FIG. 1.

As shown in FIGS. 1 and 2, the sling portion of the slouch correction device is a textile sling that is placed on a chair seat (possibly a wheelchair or other seat in which a patient may be seated for extended periods) before the patient is seated in such chair. In this example, the sling portion comprises nylon webbing supports 2 that are sewn to a fabric body 1, to form a sling or seat cover portion, and fabric straps 3, having interconnections 4 and 5, as the rearward straps. The sling portion is designed to slide with the patient seated on the fabric body 1. Fabric straps 3 extend behind the patient and are fed past the uprights of the seat of the chair, interconnections 4 and 5 are attached to the fabric straps 3, and may be slidably adjustable to different position along the length of the fabric straps 3. Side panels 6 provide additional robustness to the sling/seat cover, and may be fitted with handles 9 or 10 on opposite sides of the seat, and can be used to position the device on the seat or adjust the patient. A fore handle 8 and an aft handle 7 may also be provided, but are not necessary.

Ancillary straps 7, 8, 9 and 10 may be used to position the device on the chair, or to perform two person lifts, if desired. The lateral ancillary straps 9 and 10 are shown affixed to lateral fabric wings 6. In a basic design, the wings and ancillary straps are not needed. The overall design and the preferred method of operation allows the caregiver to keep their spine aligned and use their leg and arm muscles to readjust the patient in the seat of the wheel chair. Using this method and the device disclosed herein, a single caregiver is able to reposition the patient without placing undue strain on their back and further, the harness system provides improved leverage to reposition the patient. Further, the care giver does not need to directly touch the patient.

Figure 3:
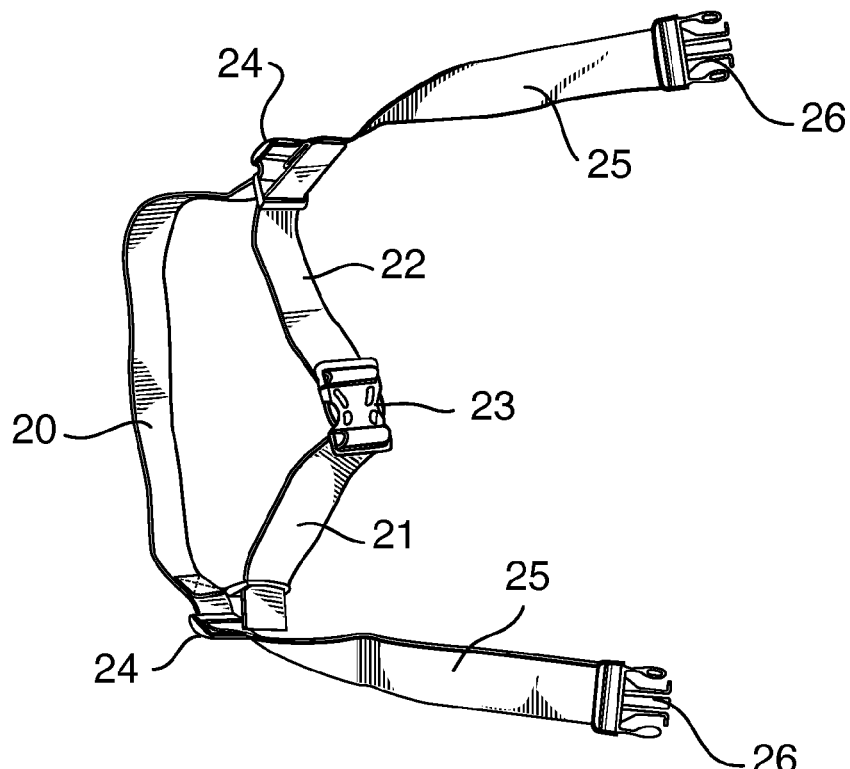
FIG. 3 is a perspective view of one example of a harness portion of the slouch correction device interoperable with the sling/seat cover portion of the slouch correction device of FIG. 1.

As shown in FIG. 3, a belt or harness that is made of fabric straps 20, 21, 22, and 25, and is fitted with adjustable clips 24 on each side and an adjustable clip 23 in front, which facilitate the fitting of the belt around a caregiver. The straps 25 protrude from each of the lateral adjustable clips 24 belt, and are each fitted with interconnections 26, to mate with interconnections 4 and 5 on the sling/seat cover portion of FIGS. 1 and 2. Adjusting the clips 24 and 23, tighten the belt/harness about the caregiver. Slidably adjusting the position of interconnections 26 on protruding lateral straps 25 permit the straps 25 on the harness and rearward straps 3 on the sling portion, to be taut during use.

Figure 4:
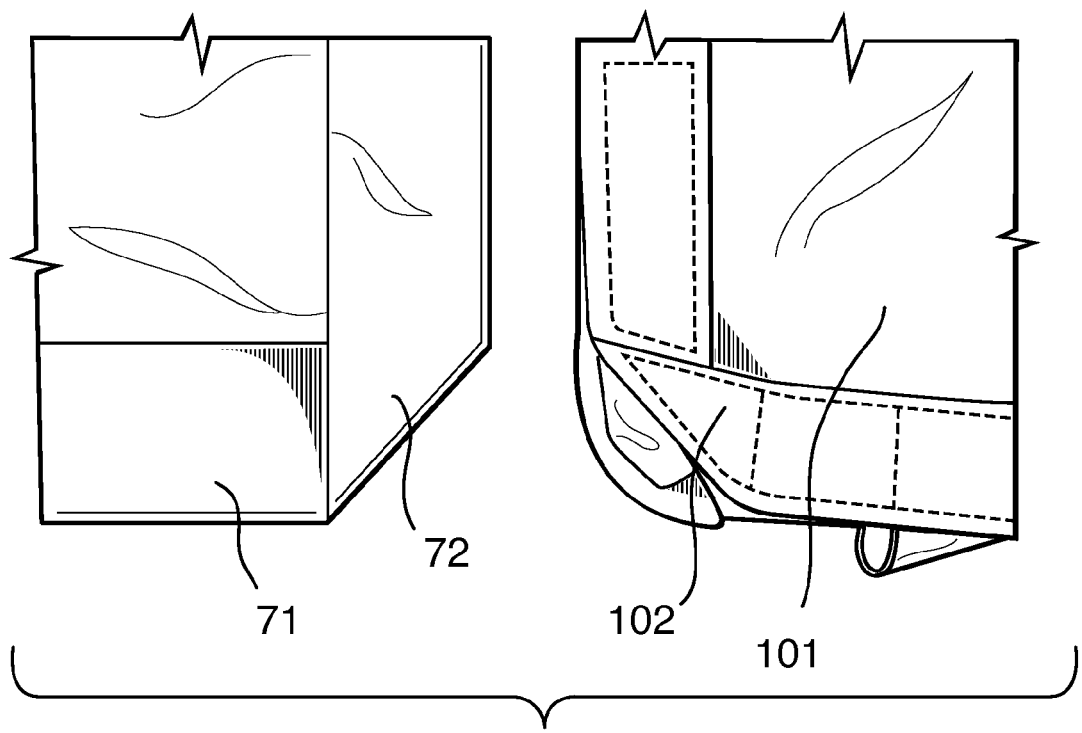
FIG. 4 shows the top view (left) and the bottom view (right) of stitching to be applied to the example of the seat cover portion of the slouch correction device of FIG. 1 as compared to the sling/seat cover portion of the slouch correction device of FIG. 5.

FIG. 4 shows alternate stitching patterns to form the edging of the sling. In the left side panel of FIG. 4, a single piece of high strength, low stretch, nylon, strapping 71 is folded and adhered to the sling material with single stitches 72. In the right side panel of FIG. 4, a narrower gage of high strength nylon strapping 101 is folded and adhered to the sling with patterned stitches 102 for additional strength. The design changes of the seat improve durability of the product. The optional chamfered edges may make the device more visually appealing and avoid discomfort of 90 degree edges on a patient. The left side panel may also feature two braces running across the bottom of the seat to provide durability. The design on the right side panel is sufficiently durable to eliminate these braces. Forming the sling from 3 pieces stitched together, instead of 1 cut piece, shortens manufacturing time and reduces material waste. The three piece design permits 90 degree corners in the sling.

EXAMPLE 2

Figure 5:
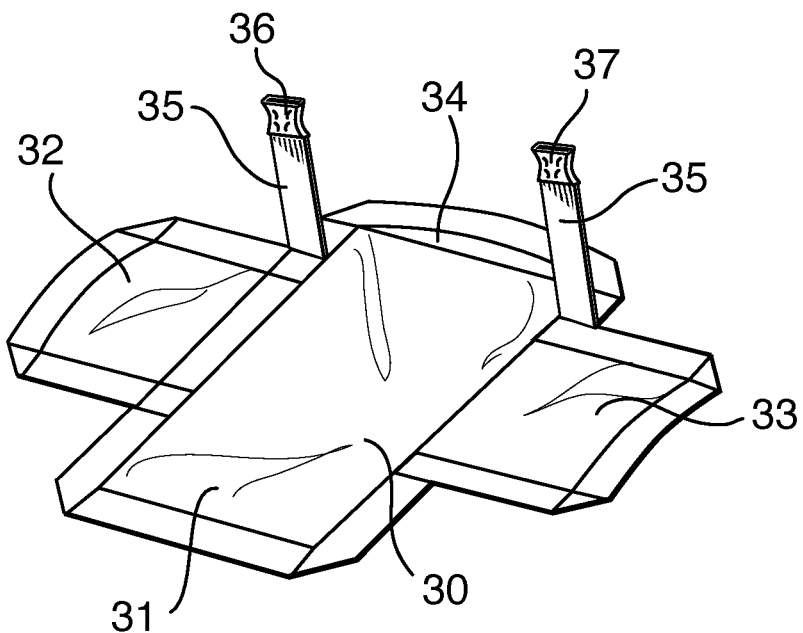
FIG. 5 is a perspective view of a second example of the sling/seat cover portion of the slouch correction device.
Figure 6:
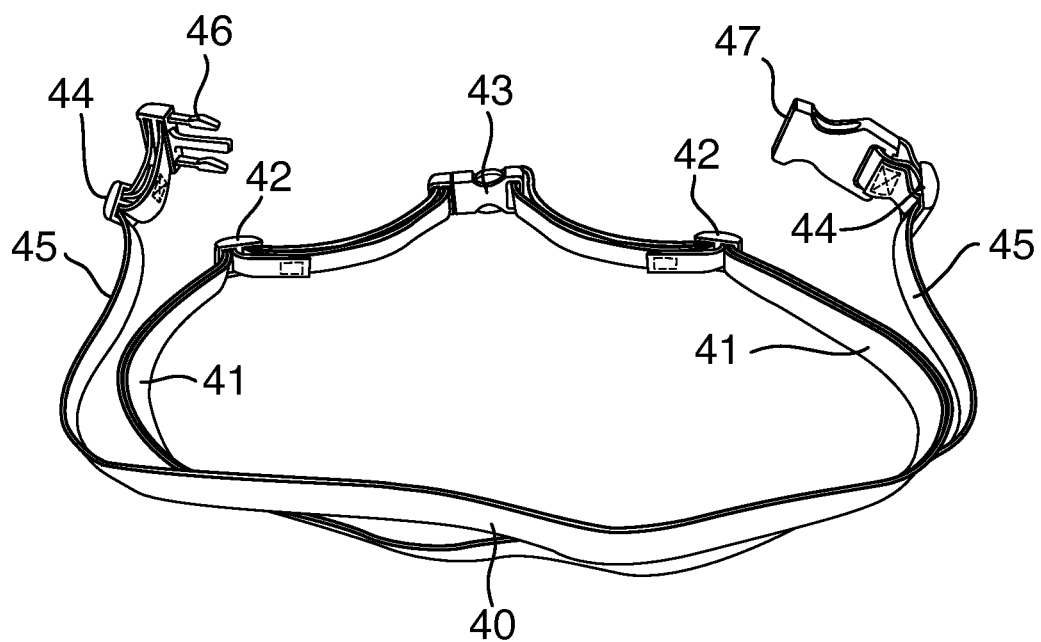
FIG. 6 is a perspective view a second example of a harness portion of the slouch correction device interoperable with the sling/seat cover portion of the slouch correction device of FIG. 5.

In a second preferred embodiment shown in FIGS. 5 and 6, the fabric straps 41 of the belt/harness 40 of FIG. 6 have both a male interconnection 46 and a female interconnection 47 to correspond to and interconnect with the female interconnection 36 and the male interconnection 37 on the straps 35 of the sling 30 of FIG. 5. Ancillary straps 31, 32, 33 and 34 of FIG.

5 are optional. In other respects, the lateral straps 45, and the adjustable clips 42, 43 and 44 of the second embodiment, operate to adjust the size of the belt/harness 40, and to permit the assembled device to be drawn taut in operation without leaning too far away from the wheelchair.

The ideology of the design is simplicity. Therefore the belt/harness 40 of FIG. 6 also differs from the belt/harness 20 of FIG. 3 by using colour and size coding to improve usability. The lateral straps 45 of the belt/harness 40 can be made of a different colour high strength, low stretch, nylon strapping which matches the rearward straps on the sling. In the second embodiment, the design colors help distinguish which part is to be attached around the waist and which part is to be attached to the seat of the device. The webbing that goes around the caregiver's waist is also a different size then the webbing that attaches to the seat of the device. This was done so the buckles could be different a size to further differentiate waist tightening from later strap shortening, and so that a waist buckle on the harness would not clip to interconnections on the seat.

There are advantages to the second embodiment over the first embodiment. Using male and female clips on the sling permits the portions to be clipped together while not performing posture correction. In this fashion, the rearward straps will not hang low and create a hazard. Clipping the interconnections of the sling together during washing also reduces damage and extends useful life of the device.

Operation

Figure 7:
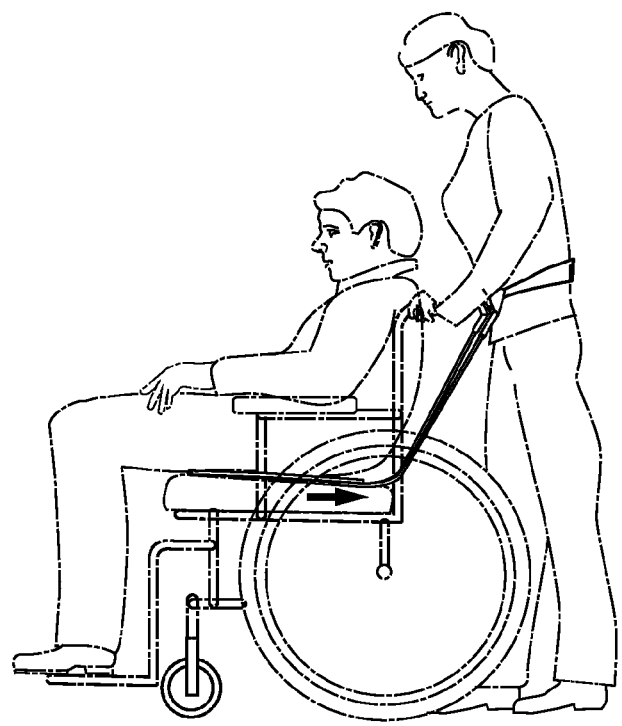
FIG. 7 is a drawing of a side view of the slouch correction device in use, with a patient slouching in a wheelchair and a caregiver in a starting operable position.
Figure 8:
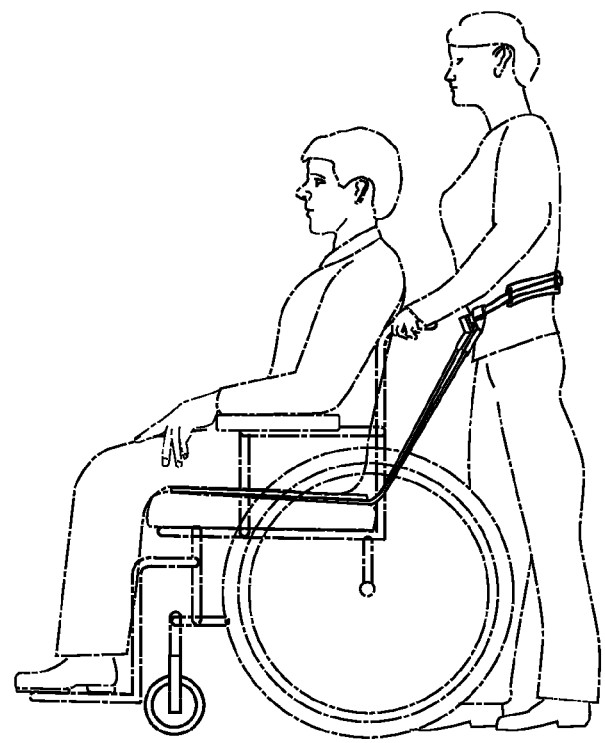
FIG. 8 is a drawing of a side view of the slouch correction device of FIG. 7, following use, with the patient no longer slouching and the caregiver in a finishing operable position.

FIG. 7 and FIG. 8 show the basic operation for the device.

In use, to reposition a slouching patient using this slouch correction device, the caregiver locks the brakes on the wheelchair, wears the harness portion of the and positions themselves behind the wheel chair. The patient will be sitting upon the sling/seat cover portion, with the fabric straps 3 (assuming the device of FIGS. 1 through 3) extending beyond the rear uprights of the wheel chair. The interconnections 26 (either male or female) of the harness mates with the interconnections 4 and 5 (corresponding to the clips on the belt). The caregiver then leans the patient slightly forward and places the patient's own hands in his/her lap. Then, the care giver either holds other handles 7 on the slouch correcting device in front of the seat back of a locked wheel chair, or the wheel chair itself to begin sliding the patient into position. The caregiver uses leg and arm strength, and their own body weight, to pull/slide the patient back into an upright posture by leaning against the belt and holding the wheel chair in position.

The operation of the device requires forces according to the following basic equation.

$$F_f = \mu F_N$$

Where: $F_f$=Force of friction, $\mu$=Coefficient of friction, $F_N$=Force normal from the patient's weight.

Figure 9:
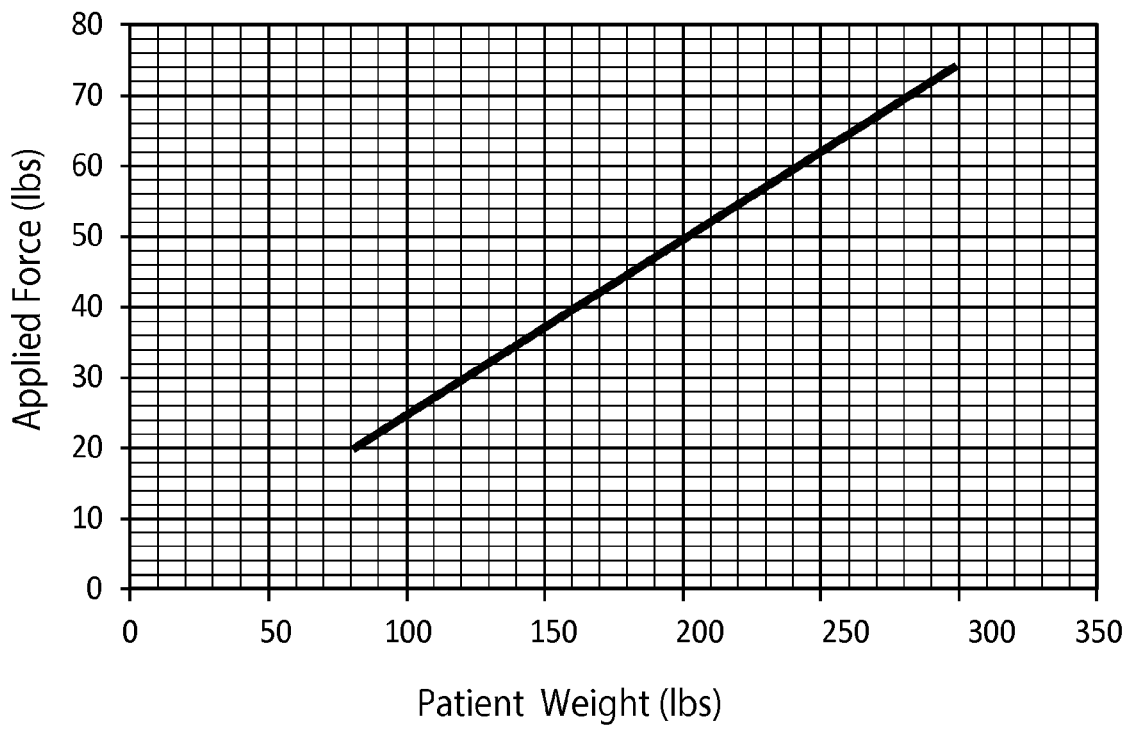
FIG. 9 is a chart demonstrating the relationship between the Applied Force (lbs) of the caregiver and the Patient Weight (lbs).
Figure 10:
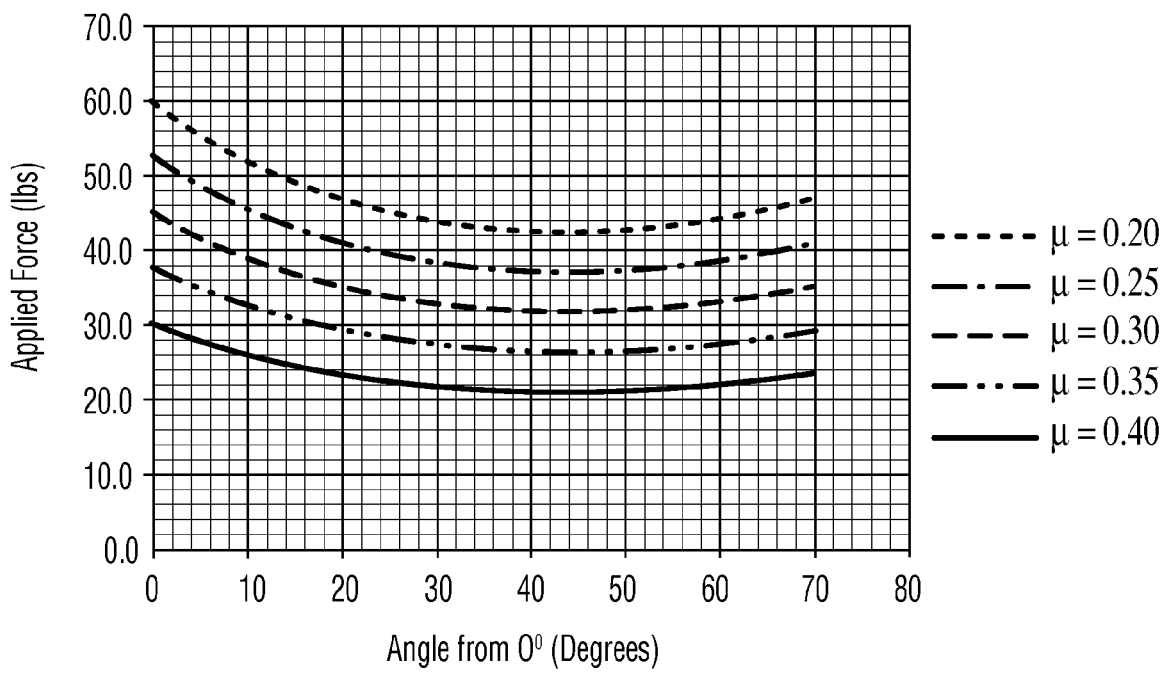
FIG. 10 is a chart demonstrating the relationship between the Applied Force (lbs) of the caregiver and the Angle from 0° (Degrees) the caregiver pulls the patient.

The force that the caregiver must apply is proportional to the coefficient of friction of the materials that are sliding against each other and the weight of the patient, and is shown in FIG. 9. By design, the coefficient of friction between the chair seat and the bottom side of the sling in the rearward direction is chosen to ensure that the applied force required is much less than the weight of the patient. To discourage excess sliding and forward slouching, the coefficient of friction between the chair seat and the bottom side of the sling in the forward direction should not be too low, but should also be less than the expected coefficient of friction between the top side of the sling and the patient. FIG. 10 shows the relationship between the required applied force for a given patient weight and angle at which for force is applied for different co-efficients of friction. In FIG. 9, the assumptions being made are the coefficient of friction is 0.35 and the angle at which the force is being pulled at 45 degrees from below the centre of mass of the patient. The device improves the opportunity for a caregiver to apply the force using large muscles in the appropriate direction, without bending.

EXAMPLE 3

As shown in FIGS. 11 through 14, various optional design improvements can be proposed to a slouch correction device of the type discussed herein, including: Velcro to keep the straps out of the way when not in use, longer straps to permit ladder lock buckles to connect straps to the harness, neoprene covering on the belt to make it more comfortable, double lateral handles to facilitate two person lifts.

Figure 11:
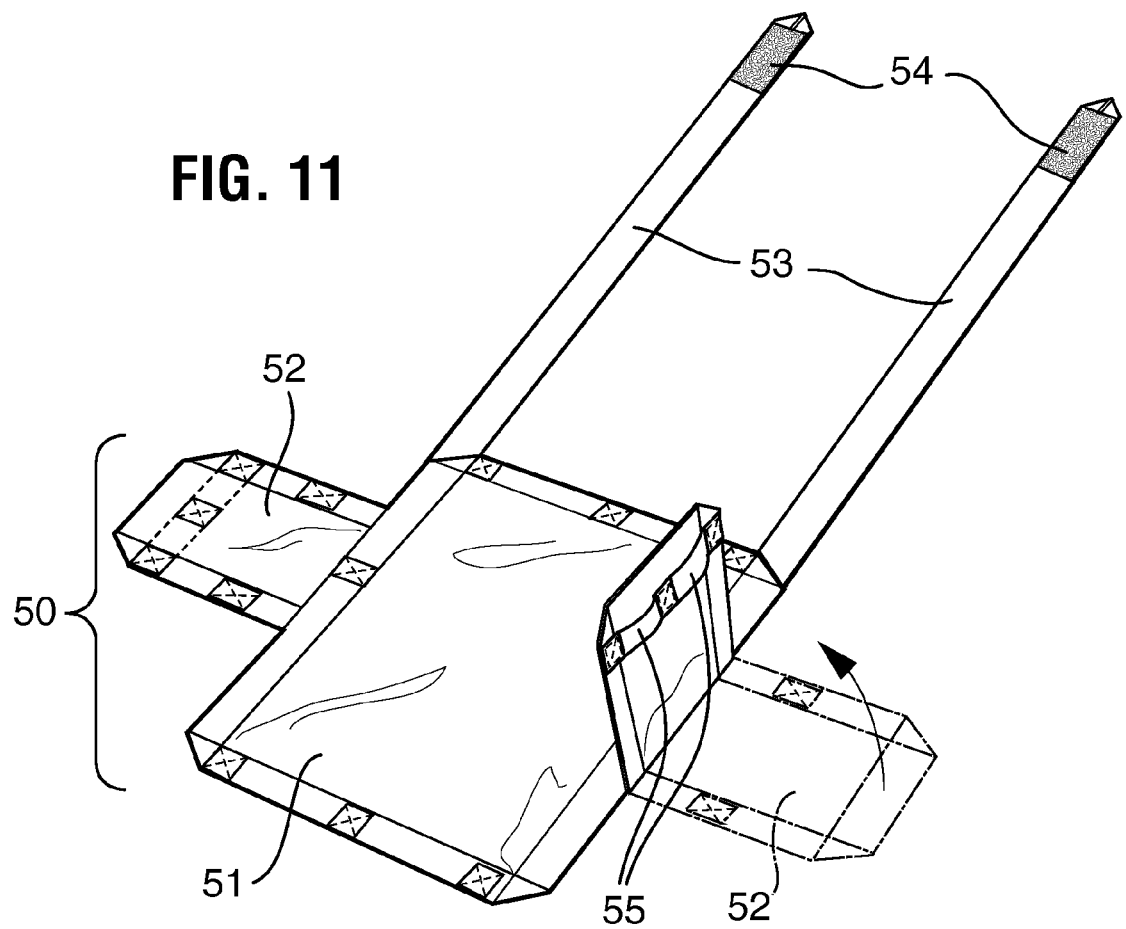
FIG. 11 is a top view of a third example of the sling/seat cover portion of the slouch correction device, [showing longer length, showing the taper, arrow shaped ends of the straps to facilitate passing them through a ladder lock buckle on the harness portion of the slouch correction device.]

As shown in FIG. 11, the sling/seat cover portion of the slouch correction device is comprised of a seat cover portion 51, side portions 52 and rearward extending straps 53. The straps 53 have tapered ends to facilitate use with ladder lock style connectors, and also have means to connect the straps to the chair on which wth device is used (Velcro 54 in the example shown, although any detachable connection could be used, including another ladder lock style buckle).

Dual handles 55 at each lift position are more ergonic for two person lifts. In the fourth example, there are dual handles at the side positions, and the fore and aft handles are omitted. The aid is better suited for a person's natural body mechanics while repositioning a patient.

Figure 12:
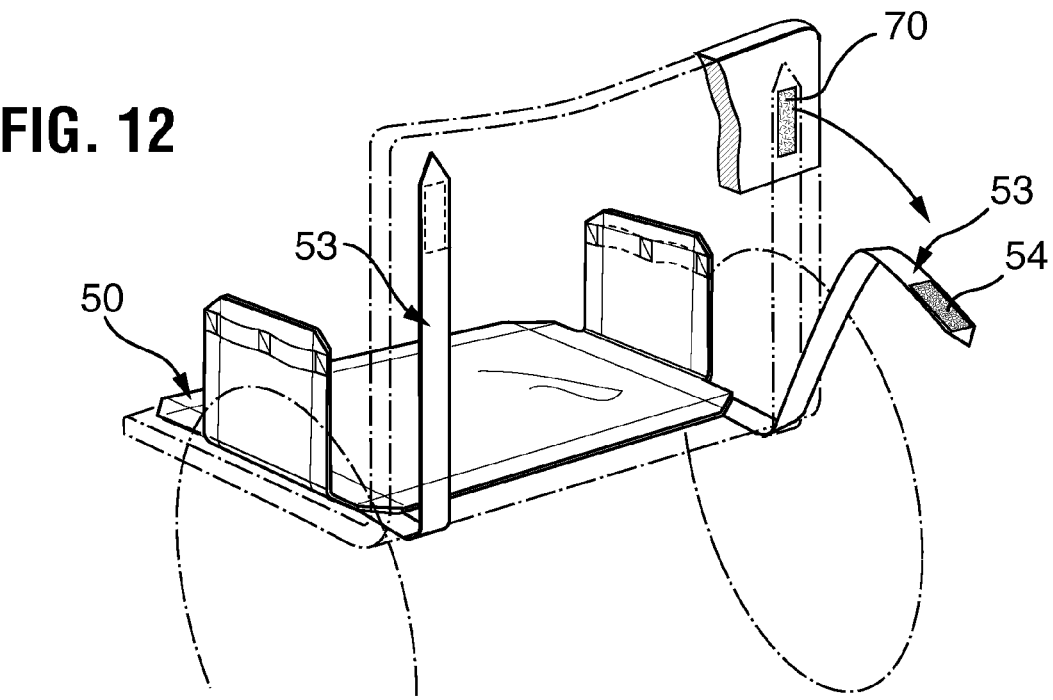
FIG. 12 is a perspective view of the sling/seat cover portion of the third example of the slouch correction device of FIG. 11 placed on a chair with straps attached by Velcro to the back of the chair.

FIG. 12 shows the chair modified to include a mating connector 70 for the straps 53. In the example shown, the Velcro 54 of the straps 53 attached to the Velcro 70 which has been previously attached to the chair to use this optional feature of the device. The straps can be detachably attached to the back of a chair, such that the caregivers no longer need to bend over to grasp the straps to fasten the aid, since they are able to stand straight and easily access the straps away the top of the chair. Stowing the straps in this fashion makes the device more safe, further reducing the risk of injury.

Figure 13:
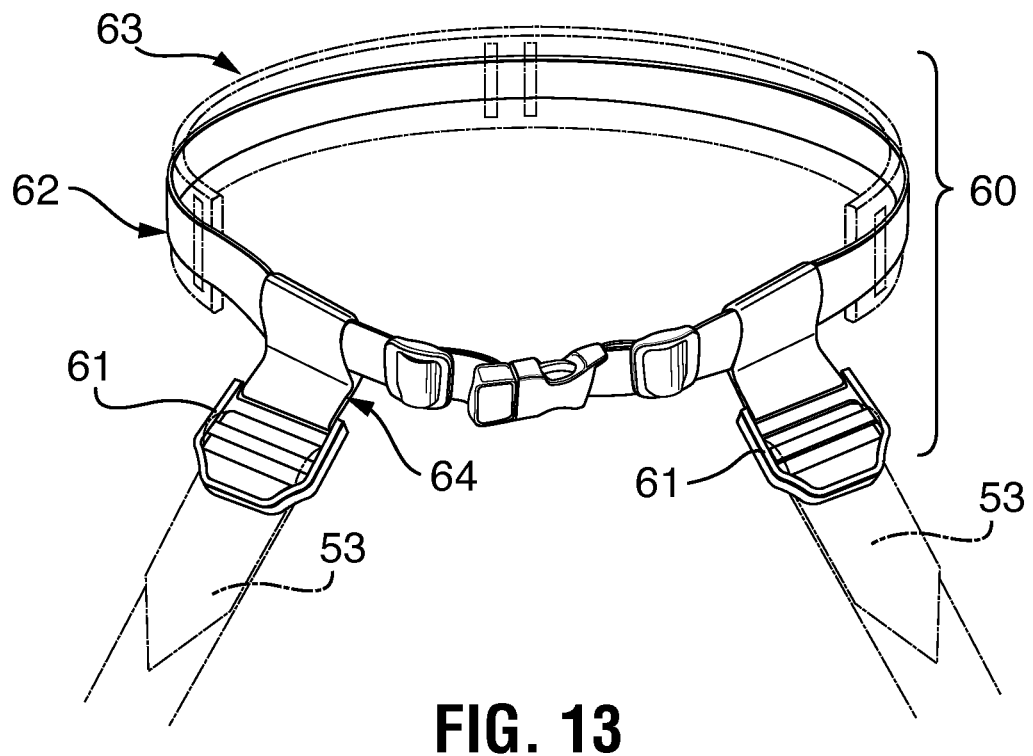
FIG. 13 is a perspective view of the harness portion of the third embodiment of the slouch correction device of FIG. 11 showing neoprene padding to provide wider and more cushioned support for a user and ladder lock buckles used to attach the straps to the belt/harness.
Figure 14:
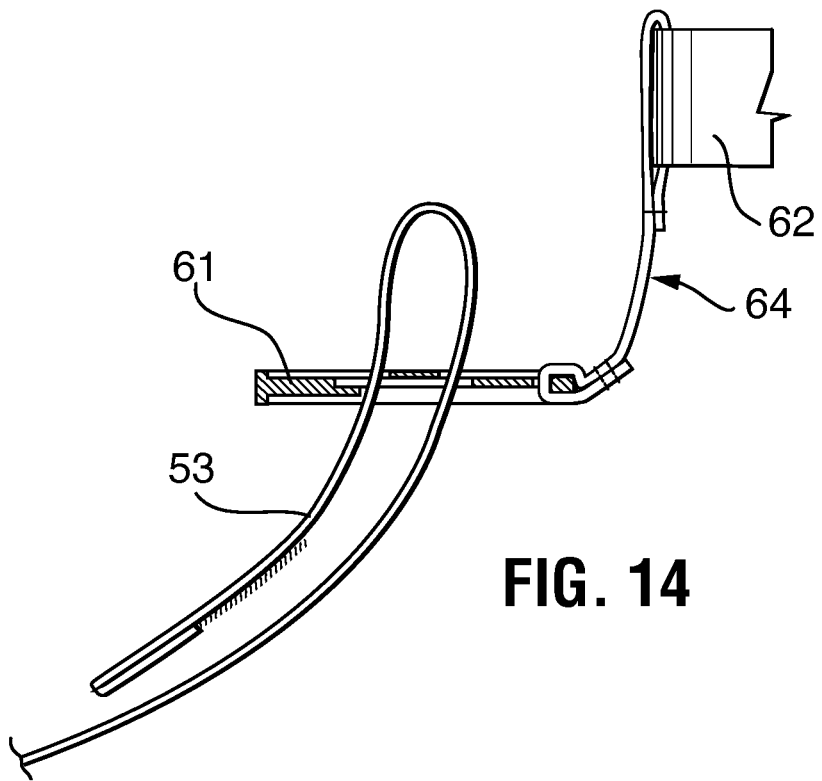
FIG. 14 is a cross section view of a the rearward straps of the sling/seat cover portion of FIG. 13 thread through the ladder lock clip of the harness portion of FIG. 13.

FIG. 13 shows a harness 60 for use as part of the third example of the aid, in which longer straps can be used with the ladder lock buckle 61 attached to a belt 62, which is also provided with a neoprene belt cover 63, making it more comfortable. Using ladder lock buckle to connect the straps to the harness, make it easier for caregivers to adjust the straps before, during and after the repositioning of a patient. The strap length on the sling/seat cover portion of the aid can be lengthened so the straps are able to work with ladder lock buckles.

The foregoing embodiments and advantages are merely exemplary and are not to be construed as limiting the scope of protection sought for the invention disclosed herein. The description of the embodiments of the slouch correction device disclosed herein is intended to be illustrative, and not to limit the scope of the claims, and many alternatives, modifications, and variations will be apparent to those skilled in the art.

The invention claimed is:
1. A slouch correction device comprising:
(a) A seat cover for the portion of a chair on which a patient, whose posture is to be adjusted by a caregiver, could sit, having one or more rearward straps;
(b) A harness to be worn by the caregiver detachably attachable to the one or more rearward straps; wherein

(c) the seat cover portion is connected laterally on each side to side panels to form a sling, the side panels each having two handles to facilitate a two person lift.

2. The slouch correction device of claim 1 in which:
(a) the seat cover portion is a textile mat with lateral reinforced edges connected to the one or more rearward straps;
(b) the one or more rearward straps further comprise one or more harness interconnections slideably positioned on the one or more rearward straps; and
(c) the harness further comprises one or more strap interconnections, detachably attached to the one or more harness interconnections.

3. The slouch correction device of claim 2 wherein:
(a) the one or more harness interconnections are slideably positioned along the one or more rearward straps;
(b) the harness is an adjustable belt having lateral straps supporting the one or more strap interconnections which are slideably positioned along the lateral straps; and
(c) The straps may be tightened by adjusting the position of the harness interconnections along the one or more rearward straps.

4. A slouch correction device comprising:
(a) A seat cover for the portion of a chair on which a patient, whose posture is to be adjusted by a caregiver, could sit, having one or more rearward straps and side panels attached laterally to the seat cover;
(b) A harness to be worn by the caregiver detachably attachable to the one or more rearward straps;
(c) for use by a patient seated on a wheelchair having a wheelchair seat, wheelchair back and dorsal opening between the wheelchair seat and wheel chair back, and by a caregiver, such that when the seat cover is placed operably on the wheelchair seat with rearward straps passed through the dorsal opening, a patient seated on the seat cover portion may be slid from a forward slouch position to an upright position, by the caregiver wearing the harness, attaching the rearward straps to the harness, holding the wheelchair and pulling rearward with the harness.

5. The slouch correction device of claim 4 wherein the side panels each have one or more handles to permit a two person lift.

6. The slouch correction device of claim 4 having two side panels, attached on opposing sides of the seat cover adjacent to the rearward straps, each side panel having two handles to facilitate a two person lift by two caregivers of a patient seated upon the seat cover portion.

7. A slouch correction device for use by a patient seated on a chair having a chair seat, chair back and dorsal opening between the chair seat and chair back, and by a caregiver comprising:
(a) A seat cover portion for positioning in an operable position on the chair seat, on which the patient, whose posture is to be adjusted by the caregiver, could sit, the seat cover portion connected laterally on each side to side panels to form a sling, the side panels each having two handles to facilitate a two person lift; and
(b) A harness worn by the caregiver attached to the seat cover portion by one or more straps which, in the operable position, pass through the dorsal opening; such that
(c) The caregiver may pull rearwards while wearing the harness and thereby slide the patient from a forward slouch position to an upright position.

8. A slouch correction device of claim 7 wherein:
(a) The seat cover portion has a top side and a bottom side; and
(b) A first expected coefficient of friction between the top side and the patient is greater than a second expected coefficient of friction between the bottom side and the chair seat such that the bottom side will slide more easily over the chair seat than the top side will slide under the patient.

9. A method by which a caregiver may adjust posture of a patient seated on a chair having a chair seat, chair back and dorsal opening between the chair seat and chair back, from a forward slouching position to an upright position comprising the steps of:
(a) Positioning a slouch correction device in an operable position on the chair seat, with a top side of a seat cover portion of slouch correction device facing upward when in the operable position on the chair seat, and one or more rearward straps of the slouch correction device passing through the dorsal opening, with the patient seated on the seat cover portion;
(b) should the patient slide into the forward slouching position, the caregiver, standing behind chair, attaching the rearward straps to a harness worn about the body of the caregiver;
(c) Adjusting the rearward straps and harness taut;
(d) holding the chair back with hands; and
(e) using leg muscles to pull slouch correction device and patient seated thereon rearward.

10. The method of claim 9 wherein the slouch correction device further comprises a top surface which does not readily slide against fabric, and a bottom surface which slides against the surface of the chair.

11. The method of claim 9 wherein the slouch correction device further comprises two rearward straps provided with chamfered ends to each pass through ladder lock buckles on the harness, and attachment means to detachably attach to attachment means on the chair when the slouch correction device is not being used by a caregiver.

12. The slouch correction device of claim 4 further comprising wheelchair attachments to be affixed to the wheelchair back above the dorsal opening, which wheelchair attachments are detachably attachable to the rearward straps such that the caregiver may detach the rearward straps from the wheelchair attachments for attachment to the harness for use and may detach the rearward straps from the harness for attachment to the wheelchair attachments for storage.

* * * * *